(12) United States Patent
Pilloni et al.

(10) Patent No.: US 11,649,478 B2
(45) Date of Patent: May 16, 2023

(54) IDENTIFICATION OF HOT ENVIRONMENTS USING BIOMARKERS FROM COLD-SHOCK PROTEINS OF THERMOPHILIC AND HYPERTHERMOPHILIC MICROORGANISMS

(71) Applicant: ExxonMobil Technology and Engineering Company, Annandale, NJ (US)

(72) Inventors: Giovanni Pilloni, Jersey City, NJ (US); Zarath M. Summers, High Bridge, NJ (US)

(73) Assignee: ExxonMobil Technology and Engineering Company, Annandale, NJ (US)

(*) Notice: Subject to any disclaimer, the term of this patent is extended or adjusted under 35 U.S.C. 154(b) by 1022 days.

(21) Appl. No.: 16/407,446

(22) Filed: May 9, 2019

(65) Prior Publication Data

US 2019/0352694 A1 Nov. 21, 2019

Related U.S. Application Data

(60) Provisional application No. 62/674,223, filed on May 21, 2018.

(51) Int. Cl.
*C12Q 1/64* (2006.01)
*C12Q 1/689* (2018.01)
(Continued)

(52) U.S. Cl.
CPC ............. *C12Q 1/64* (2013.01); *C12Q 1/689* (2013.01); *E21B 49/0875* (2020.05); *G01N 1/02* (2013.01);
(Continued)

(58) Field of Classification Search
CPC .. C12Q 1/6888; C12Q 2600/158; C12Q 1/64; C12Q 1/689; C12Q 1/6806;
(Continued)

(56) References Cited

U.S. PATENT DOCUMENTS 7,565,243 B2* 7/2009 Kim ................. G01V 1/302
702/182
8,071,295 B2* 12/2011 Ashby ................. C12Q 1/683
536/23.1
(Continued)

FOREIGN PATENT DOCUMENTS

CN 102154453 A 8/2011
CN 104630336 A 5/2015
(Continued)

OTHER PUBLICATIONS

Lazar et al., "Distribution of Anaerobic Methane-Oxidizing and Sulfate-Reducing Communities in the G11 Nyegga Pockmark, Norwegian Sea", Antonie van Leeuwenhoek, 2011, vol. 100, No. 4, pp. 639-653.
(Continued)

*Primary Examiner* — John Fitzgerald
*Assistant Examiner* — Gedeon M Kidanu
(74) *Attorney, Agent, or Firm* — Vorys, Sater, Seymour and Pease LLP (57) ABSTRACT

A method for identifying in situ presence of a hydrocarbon reservoir or of a pipeline leakage is disclosed. The method can include obtaining a sample from an area of interest, such as a sediment sample or water column sample near a hydrocarbon seep or near an offshore pipeline; analyzing the sample to detect nucleic acid, protein or metabolite signatures that are indicative of cold-shock response; identifying (Continued)

the relative abundance of the cold-shock signatures present in the sample in comparison to the surrounding environment.

10 Claims, 7 Drawing Sheets

(51) Int. Cl.
  *G01N 33/24* (2006.01)
  *G01V 9/00* (2006.01)
  *G01N 1/02* (2006.01)
  *E21B 49/08* (2006.01)
(52) U.S. Cl.
  CPC ........... *G01N 33/241* (2013.01); *G01V 9/007* (2013.01); *G01N 2001/021* (2013.01); *G01N 2570/00* (2013.01)
(58) Field of Classification Search
  CPC ............ C12Q 1/6848; C12Q 2527/125; C12Q 2565/113; C12Q 2600/156; B01D 11/0492; C12N 15/1003; C12N 15/1017; E21B 43/0122; E21B 49/08; E21B 43/00; E21B 47/11; G01V 9/007; G01V 2210/641; G01V 2210/644; G01V 99/005; G01V 1/302; G01V 1/345; G01V 11/00; G01N 33/24; G01N 33/241; G01N 33/2823; G01N 1/30; G01N 1/4077; G01N 1/42; G01N 2021/6432; G01N 21/643; G01N 21/6489; G01N 21/65; G01N 21/78; G01N 2570/00; G01N 33/28; G01N 33/6842; G01N 33/92; G06F 2111/10; G06F 30/20
  See application file for complete search history.

(56) References Cited

U.S. PATENT DOCUMENTS

| | | | | |
|---|---|---|---|---|
| 9,874,648 | B2* | 1/2018 | Braaksma | G01V 11/00 |
| 2006/0154306 | A1* | 7/2006 | Kotlar | G01V 9/007 |
| | | | | 435/6.12 |
| 2010/0279290 | A1 | 11/2010 | Sleat et al. | |
| 2011/0118983 | A1 | 5/2011 | Rowan | |
| 2012/0158306 | A1 | 6/2012 | Busche et al. | |
| 2013/0157275 | A1 | 6/2013 | Park et al. | |
| 2013/0338984 | A1* | 12/2013 | Braaksma | G01V 1/345 |
| | | | | 703/10 |
| 2014/0227723 | A1 | 8/2014 | Ingber et al. | |
| 2014/0249053 | A1* | 9/2014 | Robinson | E21B 47/11 |
| | | | | 435/6.15 |
| 2014/0315765 | A1 | 10/2014 | McDaniel et al. | |
| 2014/0378319 | A1* | 12/2014 | Regberg | C12Q 1/6888 |
| | | | | 506/9 |
| 2015/0192488 | A1 | 7/2015 | Xu et al. | |
| 2015/0291992 | A1 | 10/2015 | Al-Moniee et al. | |
| 2017/0139078 | A1* | 5/2017 | Knight | G16B 10/00 |
| 2017/0342467 | A1* | 11/2017 | Regberg | C12Q 1/689 |
| 2018/0003690 | A1* | 1/2018 | Summers | G01N 33/2823 |
| 2018/0003691 | A1* | 1/2018 | N'Guessan | G01N 33/24 |

FOREIGN PATENT DOCUMENTS

| | | | | |
|---|---|---|---|---|
| CN | 104651350 A | | 5/2015 | |
| GB | 2478511 A | | 9/2011 | |
| WO | WO-2007106244 A2 * | | 9/2007 | ............ E21B 47/00 |
| WO | 2010109173 A1 | | 9/2010 | |
| WO | 2012016215 A2 | | 2/2012 | |
| WO | WO-2013071186 A1 * | | 5/2013 | ............ B63G 8/001 |
| WO | 2013119350 A1 | | 8/2013 | |
| WO | WO-2013119350 A1 * | | 8/2013 | ............... C12Q 1/64 |
| WO | 2015103165 A1 | | 7/2015 | |
| WO | 2015103332 A2 | | 7/2015 | |

OTHER PUBLICATIONS

Orphan et al., "Culture-Dependent and Culture-Independent Characterization of Microbial Assemblages Associated With High-Temperature Petroleum Reservoirs", Applied and Environmental Microbiology, 2000, vol. 66, No. 2, pp. 700-711.

Waldron et al., "Salinity Constraints on Subsurface Archaeal Diversity and Methanogenesis in Sedimentary Rock Rich in Organic Matter", Applied and Environmental Microbiology, 2007, vol. 73, No. 13, pp. 4171-4179.

* cited by examiner

IDENTIFICATION OF HOT ENVIRONMENTS USING BIOMARKERS FROM COLD-SHOCK PROTEINS OF THERMOPHILIC AND HYPERTHERMOPHILIC MICROORGANISMS

CROSS REFERENCE TO RELATED APPLICATIONS

This application claims priority to U.S. Provisional Application Ser. No. 62/674,223 filed May 21, 2018, which is herein incorporated by reference in its entirety The subject matter of this application is related to patent application Ser. Nos. 14/350,887, 14/350,778, 15/600,161, 15/634,798, 15/634,783, and 62/656,394, the entirety of each of which are incorporated herein by reference.

FIELD

Described herein are methods for determining whether a hydrocarbon seep is in fluid communication with or otherwise indicative of a hydrocarbon reservoir. Additionally, in another application of the method, leaks from submerged offshore pipelines are detected. In particular, the methods utilize the presence of one or more cold-shock genes identified as DNA, RNA, proteins or metabolites from microbial organisms to evaluate whether said organisms belong from a reservoir or a pipeline, rather than from the surrounding environment.

BACKGROUND

This section is intended to introduce various aspects of the art, which may be associated with exemplary embodiments of the present technological advancement. This discussion is believed to assist in providing a framework to facilitate a better understanding of particular aspects of the present technological advancement. Accordingly, it should be understood that this section should be read in this light, and not necessarily as admissions of prior art.

The exploration for and discovery of new oil reserves has become increasingly challenging and costly. Untapped reserves tend to be more difficult to identify and evaluate, and are often located subsea, which further increases the complexity and cost of discovering such reserves. Successful, efficient, and cost effective identification and evaluation of hydrocarbon-bearing reservoirs is therefore very desirable.

In marine exploration, seep detection has become an important tool to identify potential hydrocarbon resources in the subsurface. Oil and gas accumulations often leak hydrocarbons including methane, ethane, propane, butane, naphthalene, and benzene. These hydrocarbons may migrate toward the surface (i.e., the seafloor), through a variety of pathways, such as faults or fracture zones. As such, the seeps become surface expressions of subsurface geological phenomena and can be used to give an indication of the subsurface conditions. In some instances, seeps may not be directly above the accumulation from which they originate but rather have further migrated and mixed with the sea water.

Analysis of fluid and sediment samples that are collected from, in, and around hydrocarbon seeps can be used to determine the presence of a mature source rock. However, such analysis cannot confirm or disprove whether the hydrocarbon seep is also connected to a hydrocarbon reservoir. That is, in some instances, while the seep is emanating from a source rock, the source rock may not be connected to a hydrocarbon reservoir.

The microbial ecology of a hydrocarbon seep can provide additional information that may be used to characterize the hydrocarbon reservoir from which the seep emanated. That is, it may be possible to use biological information from the hydrocarbon seep for exploration and hydrocarbon characterization purposes. For example, PCT Publication No. WO 2013/119350 describes using the community function and community structure of a sample ecology from a hydrocarbon seep to determine the location of a hydrocarbon reservoir. Additionally, U.S. Patent Application Publication No. 2006/0154306 describes using genotypic analysis of a sample for the presence of thermophilic or extremophilic microorganisms and comparing the biological profile of the sample to those from reference samples to determine the type of oil, quality of oil, gas/oil ratio, depth, or migration route of the sample. Further, U.S. Pat. No. 8,071,295 describes methods for performing surveys of the genetic diversity of a population, creating a database comprising the survey information, and analyzing the information to correlate the presence of nucleic acid markers with desired parameters in a sample, where the surveys are useful in the fields of geochemical exploration, agriculture, bioremediation, environmental analysis, clinical microbiology, forensic science, and medicine.

However, much of the work used to obtain biological information from hydrocarbon systems has relied on culture-based techniques. These techniques are limited because many of the organisms, particularly those living within a hydrocarbon reservoir, are not able to be cultured. While identifying and finding microbes that have originated in the reservoir and have been transported to the surface would be ideal, it is likely that only a limited number of the microbes would possibly survive transport intact. Thus, relying on culture-based techniques may not be feasible or provide a full representation of the subsurface biodiversity.

In addition, past studies have assumed that organisms living in the subsurface are similar to those at the surface. However, recent evidence indicates that the biodiversity in the subsurface is quite complex and many the subsurface species found have not been identified previously. Thus, with increasing genetic divergence from known reference species, the use of "lab-on-a-chip" type tools (e.g., microarrays using oligonucleotide-type probes or polymerase chain reaction (PCR) methods) that require specific binding of probes to identify certain known target biological species becomes less effective. That is, many of the probe-based methods may be restricted to finding organisms that have some genetic similarity to known organisms, and therefore can potentially fail to identify a large portion of the species within a sample.

Application of microbiology-based tracers has also been used to identify whether thermogenic hydrocarbons are present, by examining where hydrocarbon degradation occurs or is associated with known functions such as bacterial sulfate reduction or reactions that alter fluid properties. However, while these methods are useful for identifying diagnostic organisms or probes associated with a particular function, they do not provide information about the in situ conditions, such as the pressure, temperature, or salinity, within the reservoir.

Additional background references may include U.S. Patent Application Publication Nos. 2010/279290, 2011/0118983, 2012/0158306, 2013/0157275, 2014/0227723, 2014/0315765, 2015/0192488, and 2015/0291992; PCT Application Publication Nos. WO 2010/109173, WO 2012/016215, WO 2015/103165, and WO 2015/103332; GB Patent Application Publication No. 2478511 A; Chinese Patent Application Publication Nos. CN 102154453, CN 104630336, and CN 104651350; Lazar et al., "Distribution of anaerobic methane-oxidizing and sulfate-reducing communities in the G11 Nyegga pockmark, Norwegian Sea, Vol. 100, No. 4, pp. 639-653 (July 2011); Orphan et al., "Culture-Dependent and Culture-Independent Characterization of Microbial Assemblages Associated with High-Temperature Petroleum Reservoirs", *Applied and Environmental Microbiology*, Vol. 66, No. 2, pp 700-711 (February 2011); and Waldron et al., "Salinity Constraints on Subsurface Archaeal Diversity and Methanogenesis in Sedimentary Rock Rich in Organic Matter", *Applied and Environmental Microbiology*, Vol. 73, No. 13, pp 4171-4179 (July 2007), each of which is hereby incorporated by reference in its entirety.

SUMMARY

A method of determining whether a hydrocarbon seep is in fluid communication with a hydrocarbon reservoir, the method including: obtaining a field sample near the hydrocarbon seep; extracting one or more of proteins or nucleic acids from the field sample; analyzing the extracted proteins or nucleic acids to identify thermophiles within the field sample that exhibit signatures that are indicative of a cold-shock response; analyzing the cold-shock response thermophiles identified in step c to identify signatures that are indicative of hydrocarbon reservoir species; and determining that the hydrocarbon seep is in fluid communication with the hydrocarbon reservoir based on the presence of the cold-shock response thermophiles in the sample near the hydrocarbon seep.

In the method, the hydrocarbon seep can be a subsea seep.

In the method, the field sample can be obtained from the water column near the hydrocarbon seep.

In the method, the field sample can be a sediment sample obtained from the seafloor near the hydrocarbon seep.

In the method, the field sample can be obtained from a location that is within a radius of 10 meters from a center of a location where the hydrocarbon seep is emanating from earth's surface.

In the method, the field sample can be obtained from a location that is within a radius of 3 meters from a center of a location where the hydrocarbon seep is emanating from earth's surface.

In the method, the cold-shock response thermophiles are analyzed to identify nucleic acid signatures that are indicative of organisms from the genus *Thermotoga*.

In the method, the nucleic acid analysis can include one or more of DNA analysis, RNA analysis, and metagenomics.

In the method, the protein analysis can include proteomics.

In the method, the recited steps can be performed for multiple seeps, and the method can further include: determining multiple paths of fluid communication between the reservoir and earth's surface; including the paths in a geologic model; generating a subsurface image from the geologic model; and causing a well to be drilled at a location derived from the geologic model.

A method of monitoring a hydrocarbon pipeline disposed in a body of water, the method including: (a) obtaining a field sample near the pipeline; (b) extracting one or more of proteins or nucleic acids from the field sample; (c) analyzing the extracted proteins or nucleic acids to identify thermophiles within the field sample that exhibit signatures that are indicative of a cold-shock response; (c) analyzing the cold-shock response thermophiles identified in step c to identify signatures that are indicative of hydrocarbon reservoir species; and (d) determining that the pipeline is leaking based on the presence of the cold-shock response thermophiles in the sample near the pipeline.

In the pipeline monitoring method, steps (a)-(e) can be performed by an autonomous underwater vehicle including an automatic sample collection and analysis device.

In the pipeline monitoring method, step (a) can be performed by an underwater vehicle, and the method can further include: collecting a plurality of samples along the pipeline with the underwater vehicle; and generating, with a computer, a map of relative amounts of cold-shock response markers for various underwater locations.

DESCRIPTION OF THE FIGURES

While the present disclosure is susceptible to various modifications and alternative forms, specific example embodiments thereof have been shown in the drawings and are herein described in detail. It should be understood, however, that the description herein of specific example embodiments is not intended to limit the disclosure to the particular forms disclosed herein, but on the contrary, this disclosure is to cover all modifications and equivalents as defined by the appended claims. It should also be understood that the drawings are not necessarily to scale, emphasis instead being placed upon clearly illustrating principles of exemplary embodiments of the present invention. Moreover, certain dimensions may be exaggerated to help visually convey such principles.

DETAILED DESCRIPTION OF THE DISCLOSURE

Exemplary embodiments are described herein. However, to the extent that the following description is specific to a particular embodiment, this is intended to be for exemplary purposes only and simply provides a description of examples of the present technological advancement. Accordingly, the invention is not limited to the specific embodiments described below, but rather, it includes all alternatives, modifications, and equivalents falling within the true spirit and scope of the appended claims.

Overview

Described herein are methods for determining whether a hydrocarbon seep is in fluid communication with or otherwise indicative of a hydrocarbon reservoir, or whether an offshore pipeline transporting hydrocarbons is leaking. The methods described herein can include linking the presence of cold-shock genes as DNA, RNA, protein, or metabolite in the microbial community to the presence of a hydrocarbon reservoir or of a leak of hydrocarbons from a pipeline. Also, detection of microorganisms associated with hydrocarbon containing pipelines can be a leading indicator of pipeline failure.

The methods may comprise obtaining one or more samples near a hydrocarbon seep or near the pipeline. For example, the sample can be obtained within a radius of 150 meters, or 125 meters, or 100 meters, or 75 meters, or 50 meters, or 25 meters, or 20 meters, or 15 meters, or 10 meters, or 5 meters, or 3 meters, or 1 meter from the center of the location where the seep is emanating from the seafloor. The sample can be a fluid sample from the water column or, in the case of hydrocarbon seeps, a sediment sample from the sea floor.

The sample may be processed to extract the nucleic acids (DNA and/or RNA) and/or proteins and/or metabolites. The extracted nucleic acids may then be amplified and/or sequenced. Proteins can be identified by shotgun proteomics (e.g., bottom-up proteomics techniques used to identify proteins and characterize their amino acid sequence) or protein specific probes. Metabolites can be identified with liquid chromatography methods.

A signature (DNA, RNA, proteins or metabolites) extracted from fluids or sediments specific to a cold-shock response in thermophiles can be detected. Of the microbes determined to exhibit the cold-shock protein, these can be further analyzed to determine the presence of signature indicative of oil reservoir or pipeline species. For example, the amplified/sequenced nucleic acids can then be analyzed to identify genetic markers and/or signatures that are indicative of the presence of one or more microorganisms typically associated with oil reservoirs, such as those from the order Thermotogales, and in particular the family of Thermotogaceae. The community structure of the Thermotogales within the sample may then be analyzed to identify microorganisms from one or more of the genera *Defluviitoga, Fervidobacterium, Geotoga, Halanaerobium, Kosmotoga, Marinitoga, Mesotoga, Oceanotoga, Petrotoga, Thermopallium, Thermosipho*, and *Thermotoga*. In particular, the nucleic acid signature can be analyzed to determine the relative abundance of the genera *Thermotoga, Petrotoga*, and *Kosmotoga* within the sample. Similarly, the amplified/sequenced nucleic acids can then be analyzed to identify genetic markers and/or signatures that are indicative of the presence of one or more microorganisms typically associated with oil pipelines, such as those from the order Desulfovibrionales, and in particular from the family of Desulfovibrionaceae. The community structure of the Desulfovibrionales within the sample may be then analyzed to identify one or more of the genera *Desulfovibrio, Bilophila, Lawsonia, Desulfohalobium, Desulfomonas, Desulfonatronovibrio, Desulfomicrobium, Desulfonatronum*. In particular, the nucleic acid signature may be analyzed to determine the relative abundance of the genera *Desulfovibrio* and *Desulfonatronum*.

The presence of oil reservoir or pipeline species, with a cold-shock DNA, RNA, protein or metabolite overexpressed, is indicative that the seep is in fluid communication with a hydrocarbon reservoir, or that the leak is in fluid communication with the hydrocarbon fluid inside the pipeline, since those microbes migrated from a hot (e.g., the reservoir or the pipeline) to a colder environment (e.g., sea), thus expressing cold-shock genes in the form of RNA, translated proteins or metabolites. On the other hand, microorganisms autochthonous of sea, i.e., located at their optimal temperature, would not express cold shock genes. For example, the seep is determined to be in fluid communication with a hydrocarbon reservoir when the cold shock RNA, proteins or metabolites are in an amount that is at least double the amount of the cold shock RNA, proteins or metabolites in the surrounding area. Similarly, the pipeline is determined to present a leak when the cold shock RNA, proteins or metabolites are in an amount that is at least double the amount of the cold shock RNA, proteins or metabolites in the surrounding area. While this example relies upon a doubling of the cold shock RNA, protein, or metabolites, a smaller change could be used if a higher risk tolerance exists for a false positive.

Example methods described herein may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement various embodiments of an example methodology. Blocks may be combined or separated into multiple components. Furthermore, additional and/or alternative methodologies can employ additional blocks not shown herein. While the figures illustrate various actions occurring serially, it is to be appreciated that various actions could occur in series, substantially in parallel, and/or at substantially different points in time.

Definitions

Various terms as used herein are defined below. To the extent a term used in a claim is not defined below, it should be given the broadest possible definition persons in the pertinent art have given that term as reflected in at least one printed publication or issued patent.

The term "and/or" as used in a phrase such as "A and/or B" herein is intended to include "A and B", "A or B", "A", and "B".

"Amplification" is the generation of multiple copies of nucleic acid segments to enhance the analysis of very low amounts of nucleic acids. For example, amplification may be performed by a polymerase chain reaction ("PCR"), which uses a thermostable polymerase enzyme, such as the TAQ enzyme for DNA, to exponentially produce thousands or millions of copies of a DNA segment during a number of thermal cycles. During each cycle, the DNA segments produced in a previous cycle become templates for new copies of that segment. RNA analysis may be performed by reverse transcription of the RNA to create cDNA segments, which may then be amplified.

As used herein, "behavior" encompasses responses to stimuli. For example, the behavior of an organism may indicate the organism's motility, attachment (including biofilm formation), bioluminescence, mineral precipitation, spore formation, etc.

As used herein, "cold-shock response" refers to the synthesis of a protein by an organism to overcome the deleterious effects of cold-shock. Cold-shock also causes stabilization of the secondary structures in RNA. The temperature change needed to induce this response can vary from microbe to microbe. For reservoir microbes, everything that goes below their optimum at high temperature constitutes a shock.

As used herein, "community composition" refers to the composition of the organisms in the system. That is, the community composition is an indication of the types or organisms (e.g., Bacteria vs. Archaea, or species x vs. species y) that live or exist in the system.

As used herein, "community structure" refers to the abundance of each type of organism in the system. In particular, the community structure is an indication of the relative abundance of the different types of organisms in the system. For example, the community structure may indicate that the system comprises 10% bacteria and 90% archaea. In some embodiments, the community structure may look at only a subset of the organisms within the system and provide an indication of the relative abundance of certain species within the system as compared to other species within the system. For example, the community structure may indicate that the system comprises 25% species x, 40% species y, 30% species z, and 5% of unclassified species.

As used herein, "community function" refers to an indication of the types of metabolic processes the organisms within the system perform. For example, the community function may indicate that the organisms within the system are capable of hydrocarbon degradation, sulfate reduction, iron reduction, fermentation, etc.

As used herein, "DNA analysis" refers to any technique used to amplify and/or sequence DNA contained within the sample. DNA amplification can be accomplished using PCR techniques. DNA analysis may also comprise non-targeted, non-PCR based DNA sequencing (e.g., metagenomics) techniques. As a non-limiting example, DNA analysis may include sequencing the hyper-variable region of the 16S rDNA (ribosomal DNA) and using the sequencing for species identification via DNA.

As used herein, "ecology" refers to the study of the interactions between the living and non-living components of a system. In particular, the ecology of a sample includes information about the biology, microbiology, and molecular biology of components of the sample. Of particular reference herein, the ecology of a sample refers to a description of the organisms that live or exist within a sample, and may include parameters such as community composition, community structure, and community function of the organisms within the sample.

The term "field sample" refers to a sample containing material from the natural environment. Field samples include, but are not limited to, samples taken from any soil (encompassing all soil types and depths), water or liquid (encompassing freshwater aquatic or marine habitats), sediment (encompassing marine sediment, lake or river sediment, or mud sediment), or atmospheric dust or particulates. The field sample may include a multitude of species of microorganisms or a single species of microorganism. In preferred embodiments, the samples are field samples taken from the sediment or water column near a hydrocarbon seep or water near a submerged pipeline used for hydrocarbons transport. In such a context, the term "near" means the sample is obtained within a radius of 150 meters, or 125 meters, or 100 meters, or 75 meters, or 50 meters, or 25 meters, or 20 meters, or 15 meters, or 10 meters, or 5 meters, or 3 meters, or 1 meter from the center of the location where the seep is emanating from the surface or from any given location along the pipeline length. Reference samples may also be field samples taken from the sediment or water column away from the hydrocarbon seep or away from the pipeline. In such a context, the term "away" means the reference sample is obtained at least 200 meters, or at least 250 meters, or at least 300 meters, or at least 350 meters, or at least 400 meters, or at least 450 meters, or at least 500 meters away from the center of the location where the seep is emanating from the surface, and in some embodiments, less than 2000 meters, or less than 1750 meters, or less than 1500 meters, or less than 1250 meters, or less than 1000 meters away from the location where the seep is emanating from the surface. Similarly, for pipelines the term "away" means the reference sample is obtained at least 200 meters, or at least 250 meters, or at least 300 meters, or at least 350 meters, or at least 400 meters, or at least 450 meters, or at least 500 meters away from the location of the pipeline, and in some embodiments, less than 2000 meters, or less than 1750 meters, or less than 1500 meters, or less than 1250 meters, or less than 1000 meters away from the location where the pipeline is located.

"Automatic sample collection and/or analysis" is, especially for pipeline, one or more devices that can independently and continuously inspect and/or analyze the water close to the pipeline external wall or other structure and communicate the results in real time or near real time. Non-limiting examples include a submersible vehicle (either autonomous underwater vehicle (AUV) or other controlled submersible) with a water sample collection mechanism and sensors/processors that could detect and/or analyze a florescent antibody or other specific indicator of cold shock RNA, protein, or metabolite (i.e., perform metabolomics). Such vehicles can equipped with computer equipment programmed to carry out the various analyses described herein, and various microarrays.

A "geologic model" is a computer-based representation of a subsurface earth volume, such as a petroleum reservoir or a depositional basin. Geologic models may take on many different forms. Depending on the context, descriptive or static geologic models built for petroleum applications can be in the form of a 2-D or 3-D array of cells, to which geologic and/or geophysical properties such as lithology, porosity, acoustic impedance, permeability, or water saturation are assigned (such properties are referred to collectively herein as "reservoir properties"). Many geologic models are constrained by stratigraphic or structural surfaces (for example, flooding surfaces, sequence interfaces, fluid contacts, and/or faults) and boundaries (for example, facies changes). These surfaces and boundaries define regions within the model that possibly have different reservoir properties.

As used herein, "genomics" refers to the study of genomes of organisms, which includes the determination of the entire DNA or RNA sequence of organisms as well as genetic mapping.

A "hydrocarbon" is an organic compound that primarily includes the elements hydrogen and carbon, although nitrogen, sulfur, oxygen, metals, or any number of other elements may also be present in small amounts. As used herein, hydrocarbons generally refer to organic materials (e.g., natural gas and liquid petroleum) that are harvested from hydrocarbon containing sub-surface rock layers, termed reservoirs.

As used herein, "hydrocarbon management" or "managing hydrocarbons" includes hydrocarbon exploration, hydrocarbon development, hydrocarbon extraction, hydrocarbon production, identifying potential hydrocarbon resources, identifying well locations, determining well injection and/or extraction rates, identifying reservoir connectivity, acquiring, disposing of and/or abandoning hydrocarbon resources, reviewing prior hydrocarbon management decisions, and any other hydrocarbon-related acts or activities.

As used herein, "hydrocarbon exploration" refers to any activity associated with determining the location of hydrocarbons in subsurface regions. Hydrocarbon exploration normally refers to any activity conducted to obtain measurements through acquisition of measured data associated with the subsurface formation and the associated modeling of the data to identify potential locations of hydrocarbon accumulations. Accordingly, hydrocarbon exploration includes acquiring measurement data, modeling of the measurement data to form subsurface models, and determining the likely locations for hydrocarbon reservoirs within the subsurface. The measurement data may include seismic data, gravity data, magnetic data, electromagnetic data, and the like.

As used herein, "hydrocarbon development" refers to any activity associated with planning of extraction and/or access to hydrocarbons in subsurface regions. Hydrocarbon development normally refers to any activity conducted to plan for access to and/or for production of hydrocarbons from the subsurface formation and the associated modeling of the data to identify preferred development approaches and methods. By way of example, hydrocarbon development may include modeling of the subsurface formation and extraction planning for periods of production, determining and planning equipment to be utilized and techniques to be utilized in extracting the hydrocarbons from the subsurface formation, and the like.

As used herein, "hydrocarbon production" refers to any activity associated with extracting hydrocarbons from subsurface location, such as a well or other opening. Hydrocarbon production normally refers to any activity conducted to form the wellbore along with any activity in or on the well after the well is completed. Accordingly, hydrocarbon production or extraction includes not only primary hydrocarbon extraction, but also secondary and tertiary production techniques, such as the injection of gas or liquid for increasing drive pressure, mobilizing the hydrocarbon, or treating the well by, for example, chemicals, or hydraulic fracturing the wellbore to promote increased flow, well servicing, well logging, and other well and wellbore treatments.

As used herein, "metabolites" refer to compounds produced by bacteria and/or archaea during respiration or fermentation. For example, acetic acid is an example of a metabolite. Metabolites can provide information about the type of hydrocarbon being used as a substrate as well as information about physical and chemical conditions in the reservoirs. For example, the presence of specific metabolites may indicate or infer the presence of hydrocarbons and/or conditions at depth.

A "microbe" is any microorganism that is of the domain Bacteria, Eukarya, or Archaea. Microbes include bacteria, fungi, nematodes, protozoans, archaebacteria, algae, dinoflagellates, molds, bacteriophages, mycoplasma, viruses, and viroids.

As used herein, a "microarray" is a multiplex lab-on-a-chip that allows many tests to be performed simultaneously or in sequence. It is an array of hundreds to thousands of spots containing probes (or tags) of various types. Lab-on-a-chip and microfluidics devices allow for the analysis of samples using miniaturized laboratory processes, which require small sample sizes, such as less than $10^{-6}$ L of the sample, or less than $10^{-9}$ L of the sample.

The term "nucleic acid" refers to biopolymers used in cells for the transfer of information. Nucleic acids include deoxyribonucleic acid ("DNA"), which is generally found in a nucleus of a eukaryotic cell, and ribonucleic acid ("RNA"), which is generally found in the cytoplasm of a eukaryotic cell. A prokaryotic cell, such as a bacterial or archaeal cell, does not have a nucleus, and both DNA and RNA may be found in the cytoplasm of the cell. DNA often provides the genetic code for a cell, although a few types of organisms use RNA to carry heritable characteristics. RNA is often associated with the synthesis of proteins from genes on the DNA.

As used herein, "products" refer to proteins, lipids, exopolymeric substances, and other cellular components that organisms produce under a given set of conditions.

As used herein, "proteomics" refers to the description of proteins produced by bacteria and/or archaea. Proteins can be used to describe the function of the most active members of a microbial community. Proteomics can be used to describe community structure, but only if the links between individual species and expressed proteins are clearly understood. Proteins can be separated using two dimensional electrophoresis. The proteins can then be analyzed using a TOF (time of flight) mass spectrometer coupled to a liquid chromatograph or a MALDI (matrix assisted laser desorption/ionization) unit. Since proteins are not easily amplified proteomic analysis in natural samples often requires a large amount of biomass to be successful.

As used herein, "RNA analysis" refers to any technique used to amplify and/or sequence RNA contained within the samples. The same techniques used to analyze DNA can be used to amplify and sequence RNA. RNA, which is less stable than DNA is the translation of DNA in response to a stimuli. Therefore, RNA analysis may provide a more accurate picture of the metabolically active members of the community and may be used to provide information about the community function of organisms in a sample.

As used herein, "metabolomics" refers to any technique used to detect and/or characterize metabolites contained within the samples. Metabolites analysis or metabolomics is normally performed with advanced chromatography techniques in combination with statistical methods. The analysis of metabolites can provide insights into the transformations occurred and occurring in a samples, thus providing a more accurate picture of the metabolic networks between the different active members of the community.

A "reservoir" is a subsurface rock formation from which a production fluid can be produced. The rock formation may include granite, silica, carbonates, clays, and organic matter, such as oil, gas, or coal, among others. Reservoirs can vary in size from less than one cubic foot (0.3048 m$^3$) to hundreds of cubic feet (hundreds of cubic meters). The permeability of the reservoir rock may provide paths for production and for hydrocarbons to escape from the reservoir and move to the surface.

A "seep" or "hydrocarbon seep" or "petroleum seep" is a place where hydrocarbons escape to the surface, normally under low pressure or flow. Seeps may occur above either terrestrial or offshore petroleum reservoirs, but may also occur above subsurface deposits of organic material, for example, as the organic material degrades. The hydrocarbons may escape from the reservoir or deposit along geological layers, or through fractures and fissures in the rock.

A "pipeline" is a tube or system of tubes used for transporting crude oil and natural gas.

As used herein, a "sensor" is a device that detects and measures one or more physical, chemical, or biological signals.

As used herein, "sequencing" refers to the determination of the exact order of nucleotide bases in a strand of DNA (deoxyribonucleic acid) or RNA (ribonucleic acid) or the exact order of amino acids residues or peptides in a protein. For example, nucleic acid sequencing can be done using Sanger sequencing or next-generation high-throughput sequencing including but not limited to massively parallel pyrosequencing, Illumina sequencing, or SOLiD sequencing, ion semiconductor sequencing. For example, amino acid sequencing may be done by mass spectrometry and Edman degradation.

"Substantial" when used in reference to a quantity or amount of a material, or a specific characteristic thereof, refers to an amount that is sufficient to provide an effect that the material or characteristic was intended to provide. The exact degree of deviation allowable may in some cases depend on the specific context.

As used herein, "transcriptomics" refers to the amplification and/or sequencing of mRNA (messenger RNA), rRNA (ribosomal RNA), and tRNA (transfer RNA). These types of RNA are used to build and synthesize proteins. Understanding what transcripts are being used allows one to understand what proteins are being produced, and thus provides information about the community function of organisms in a sample.

Fluids and sediments collected in and around hydrocarbon seeps can be used to describe the presence of a mature source rock. Further, as described herein, the presence or absence, and relative abundance of unique microbial species within the sample can provide an indication of the in situ conditions of the hydrocarbon reservoir from which the seep emanated. That is, by analyzing the microbial signature of the sample from a hydrocarbon seep or a pipeline, one can infer that certain conditions exist in the subsurface reservoir. In particular, the presence of microbes the can survive at extreme conditions can be used as a tracer to identify hydrocarbon seeps connected to reservoirs. Further, information about the community structure and community function of the samples can be used to describe the physical conditions (e.g., temperature and pressure) and chemical conditions (e.g., salinity) of the connected hydrocarbon reservoir.

Exemplary Embodiments

Figure 1:
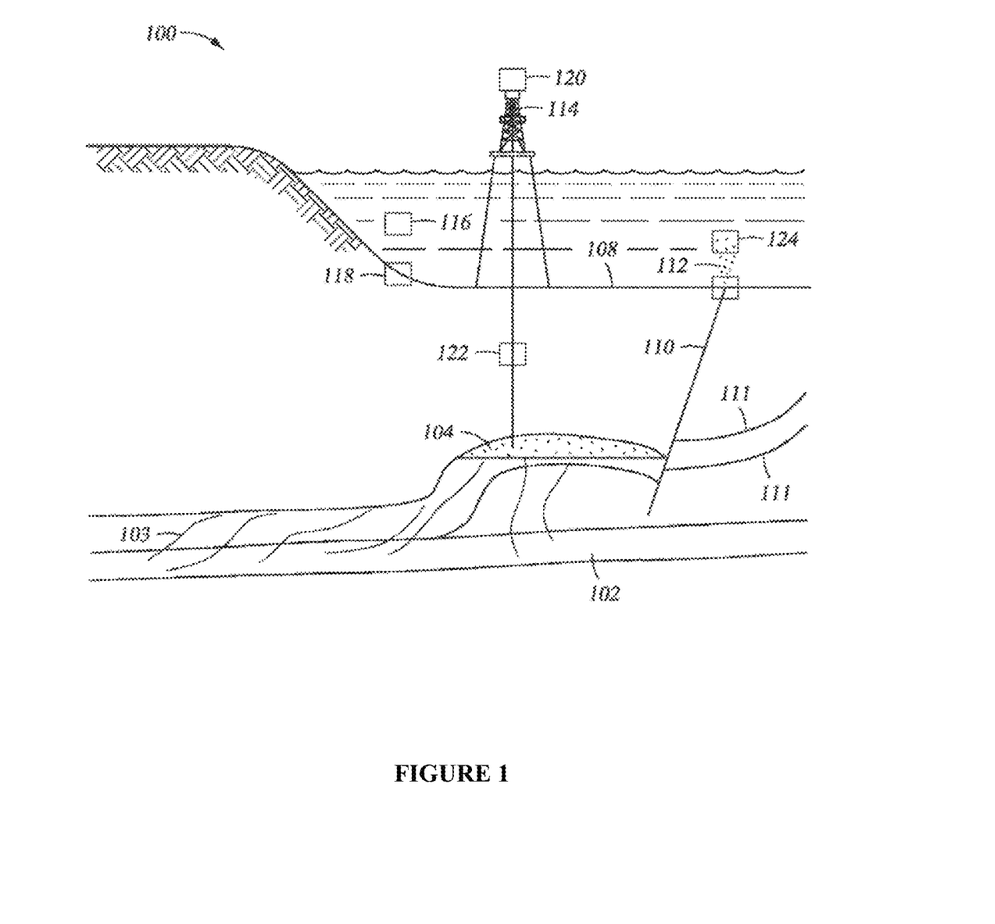
FIG. 1 is a schematic illustrating a cross section view of a hydrocarbon system and an associated seafloor seep.

FIG. 1 illustrates a hydrocarbon system 100 that includes an organic carbon bearing source rock 102 that generates and excretes liquid and gaseous hydrocarbons, which migrate through various migration pathways 103 into a reservoir 104. The hydrocarbons are trapped in the reservoir 104. A sealing interval above the reservoir prevents further hydrocarbon migration out of the reservoir. However, hydrocarbons can escape from the reservoir and migrate toward the surface (shown in FIG. 1 as a seafloor 108) through a variety of pathways, such as faults 110 or fracture zones 111. This hydrocarbon migration can then result in seeps 112 discharging hydrocarbons from the seafloor into the water column. Water samples 124 can be taken at or near a suspected seep 112 to determine the ecology of the associated water column. For example, the sample may be taken within a radius of 150 meters, or 125 meters, or 100 meters, or 75 meters, or 50 meters, or 25 meters, or 120 meters, or 15 meters, or 10 meters, or 5 meters, or 3 meters, or 1 meter, from the center of the location where the seep is emanating from the seafloor 108. A suspected seep may be identified a variety of methods, for example the presence of physical disturbance of the sediment, bubble trains, microbial mats, and oil slicks or sheens at the sea-air interface, may all indicate the presence of an active seep. To control for microorganisms present in the water that are not associated with a seep, a water sample 116 may also be taken in a region where there are no known seeps. Thus, by comparing the microbial signatures of the sample from the seep 124 and the control sample 116 one can determine which organisms have migrated from the subsurface reservoir. Other samples 118 may also be collected from shallow sediment on the seafloor to determine the ecology of the seafloor 108. Once a likely site for the hydrocarbon accumulation has been established, an exploration well 114 can be drilled and one or more core samples 122 can be taken. Likewise, liquid samples may be collected from a production platform 120. Information from the core samples or liquid samples from the production platform can be used to verify or calibrate information determined about the subsurface conditions by the methods described herein.

Figure 2A:
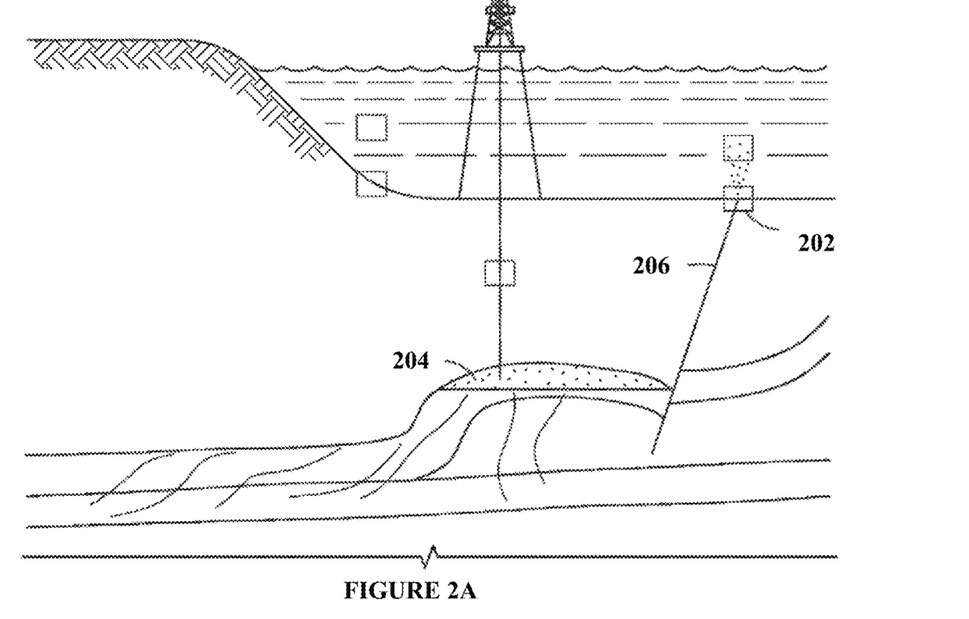
FIGS. 2A, 2B, 2C, and 2D are schematics illustrating cross section views of different types of seafloor hydrocarbon seeps.
Figure 2B:
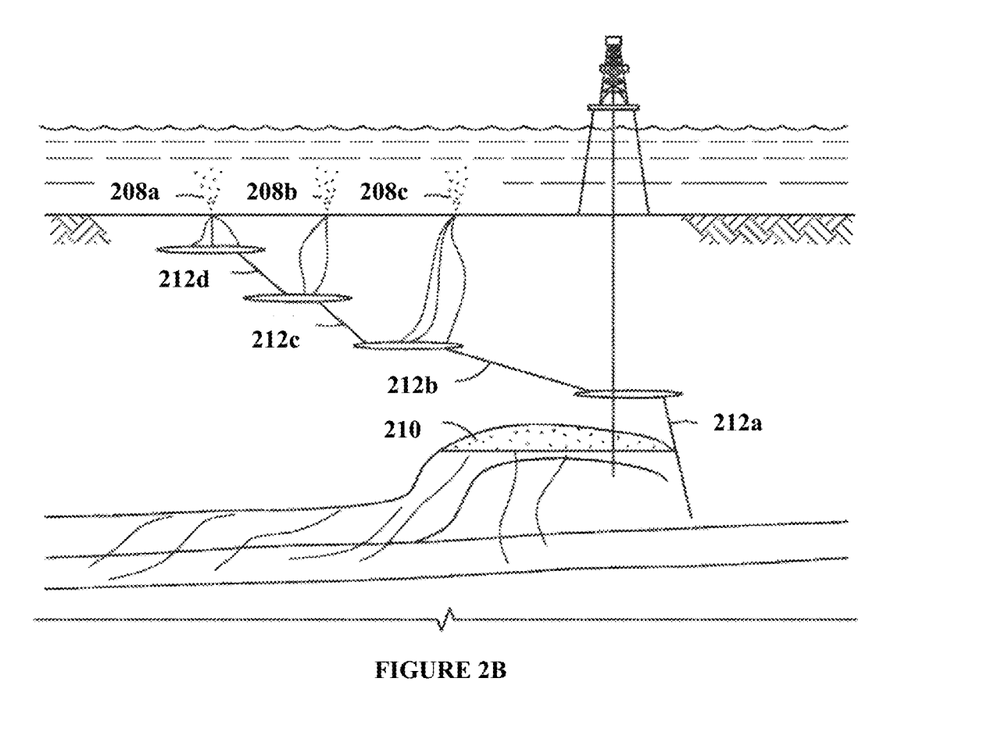
Figure 2C:
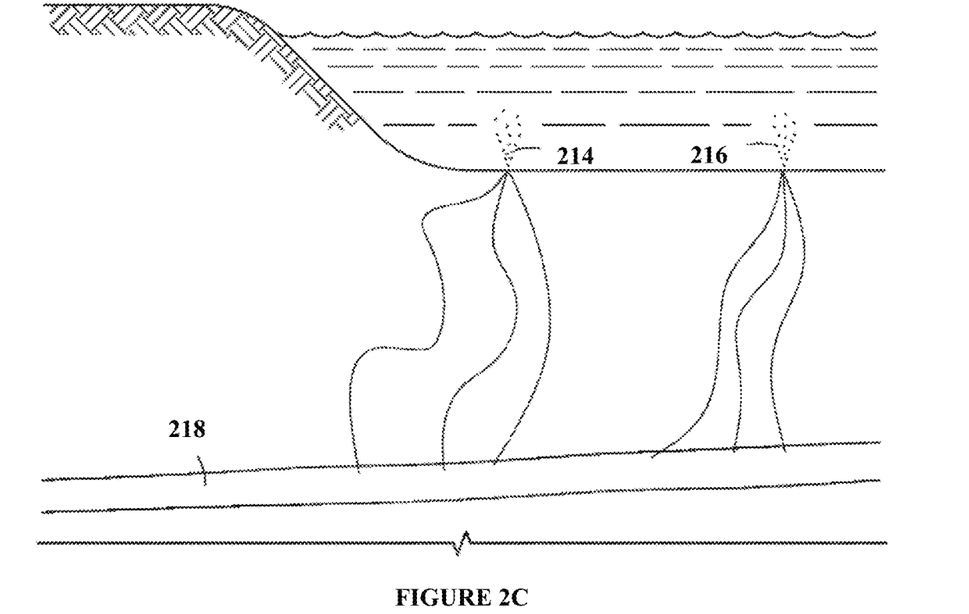
Figure 2D:
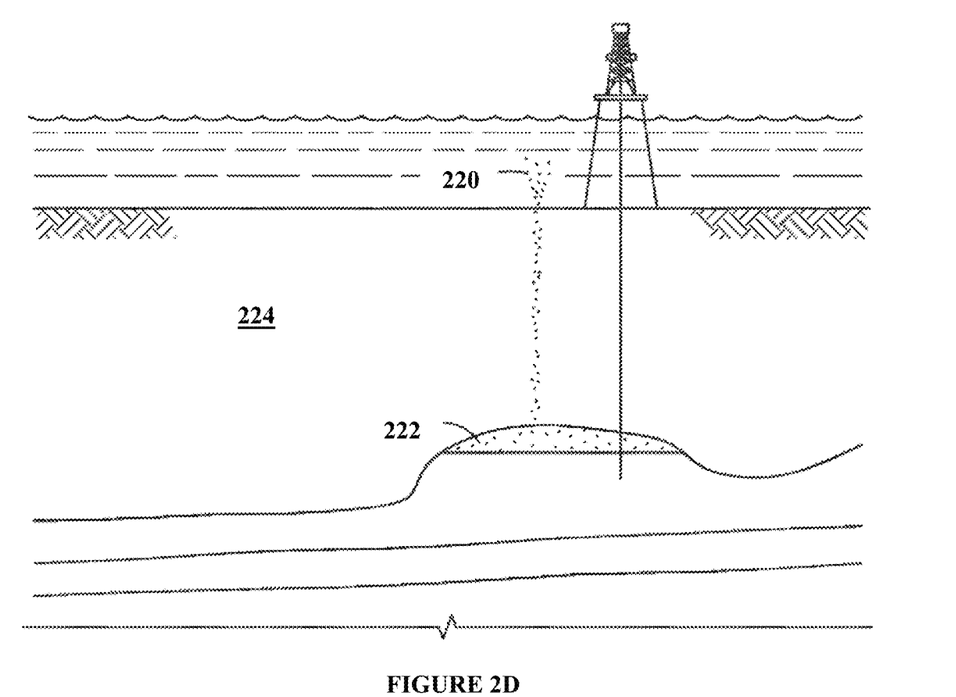

FIGS. 2A to 2D illustrate different types of seafloor hydrocarbon seeps. FIG. 2A is similar to FIG. 1, and shows a seep 202 directly connected to or in fluid communication with a hydrocarbon reservoir 204 through a fault 206. FIG. 2B shows a series of seeps 208a, 208b, 208c that are indirectly connected to, but still in fluid communication with, an hydrocarbon reservoir 210 through a series of faults 212a, 212b, 212c, 212d. FIG. 2C shows a pair of seeps 214, 216, independent of any faults that are linked to an actively generating source rock 218 in which there is no reservoir. FIG. 2D shows a fault-independent seep 220 associated with a hydrocarbon reservoir 222. In FIG. 2D, the hydrocarbons in the reservoir 222 overcome the capillary entry pressure of the overlying rock 224 and escape to the surface. As seen in FIGS. 2A to 2D, hydrocarbon seeps can have vastly different physical conditions, such as being connected to or in fluid communication with a hydrocarbon reservoir in FIGS. 2A, 2B, and 2D versus being independent of a reservoir as seen in FIG. 2C. Further, the hydrocarbon seep can directly emanating from the reservoir as in FIG. 2D, emanate from a fault connected to the reservoir as in FIG. 2A, or emanate from faults that are indirectly connected to a reservoir as in FIG. 2B. The methods and techniques described herein can be used to analyze the microbial signatures of samples taken from the hydrocarbon seep to identify physical and chemical conditions unique to each system, and thus give an indication of what kind of source the hydrocarbons in the seep have emanated from.

Physical and chemical conditions in hydrocarbon reservoirs are typically very different from conditions at the seafloor. Pressure and temperature are both generally higher in hydrocarbon reservoirs than at the seafloor. Additionally, salinity is often higher in hydrocarbon reservoirs than at the seafloor and organic carbon is more abundant in a hydrocarbon reservoir. These differences create different environments for different types of microorganism to thrive in where they otherwise would not. For example, thermophilic and halophilic bacteria have been identified and isolated from hydrocarbon reservoirs that would not normally exist at the seafloor. As these microorganisms are transported to the surface via a hydrocarbon seep they can be detected in samples from the hydrocarbon seep. Furthermore, organisms living at reservoir conditions and/or those that are transported to the seafloor express different proteins (e.g., a cold-shock protein), thereby permitting a determination of that the organisms traveled to the surface from a warmer environment indicative of a hydrocarbon reservoir. In the absence of an active hydrocarbon system, the links between the water column, seafloor sediment and subsurface ecology become less clear. Similarly, microorganisms from a pipeline, transported to the sea water express different proteins (e.g., a cold-shock protein), thereby permitting a determination that the organisms moved to the water column from a warmer environment, indicative of a leak in the pipeline.

Organisms contained in samples are characterized for various phenotypes and physiological aspects. For example, the organisms can be cultured and tested for their ability to survive and grow under a variety of environmental conditions such as pressure, temperature, salinity, etc. The ability of organisms to degrade hydrocarbons of interest may also be determined. Organisms exhibiting target characteristics are also isolated and characterized at depth. Molecular characterization typically requires the extraction of components from samples. These components include nucleic acids (e.g., DNA and RNA) and proteins. Analysis of these components requires various techniques which include nucleic acid sequencing, protein sequencing, and/or some sort of separation and/or hybridization.

According to aspects of disclosed methodologies, a method is provided for using the ecology and physiology of a sample from a hydrocarbon seep or from the proximity of a pipeline transporting hydrocarbons to determine characteristics of the subsurface hydrocarbon system. An illustrated method is provided with reference to FIG. 3. At block 302 a sample is collected from the sediment near a hydrocarbon seep or the water column associated with a hydrocarbon seep or water column in the proximity of a pipeline, or regions near a pipeline. The samples may be collected by hand, by using a remotely operated vehicle, or an AUV. Sediment samples may come from small sediments coops, push cores, box cores, gravity cores, piston cores, or jumbo piston cores. Liquid samples from the water column or from outside a pipeline may include water and hydrocarbon independently or in a mixture. The sample may be taken within a radius of 150 meters, or 125 meters, or 100 meters, or 75 meters, or 50 meters, or 25 meters, or 20 meters, or 15 meters, or 10 meters, or 5 meters, or 3 meters, or 1 meter, from the center of the location where the seep is emanating from the seafloor or from the pipeline.

Figure 3:
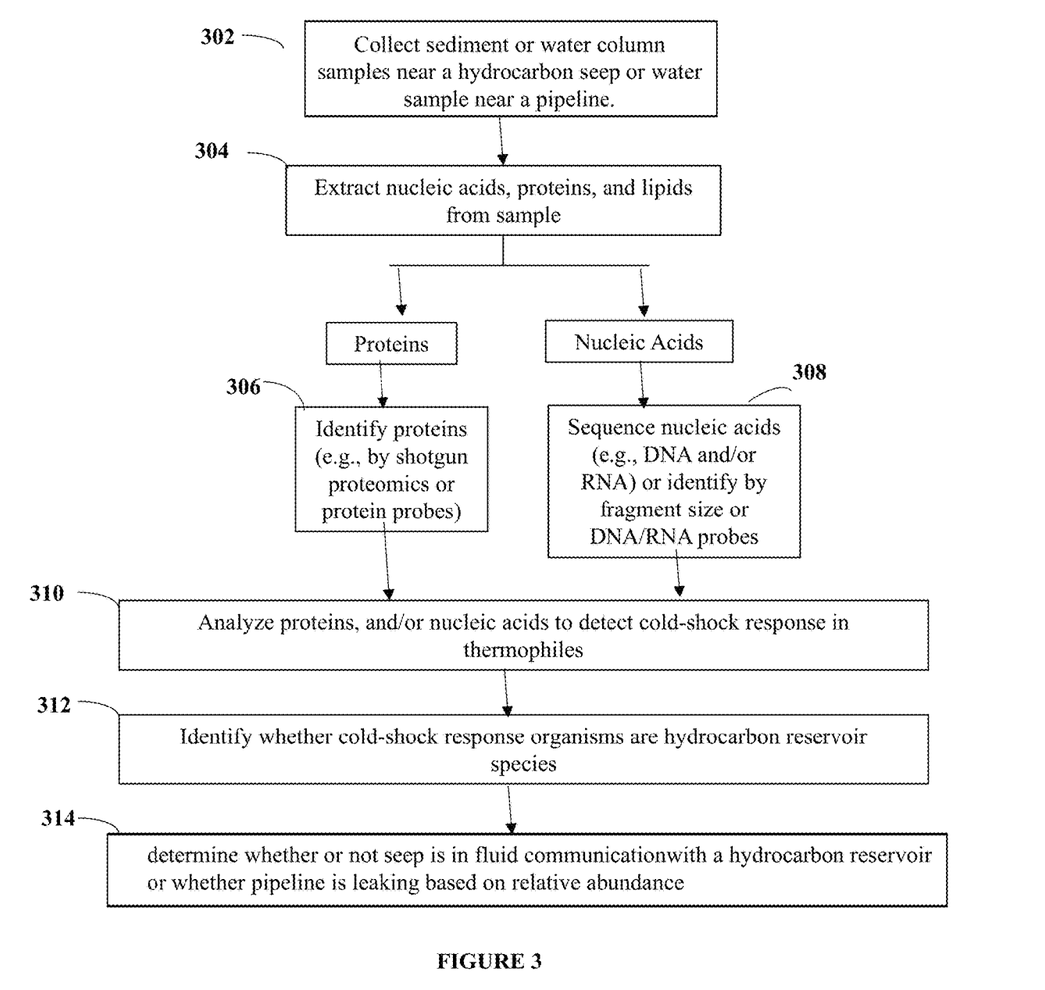
FIG. 3 is a block diagram of a workflow according to methodologies and techniques described herein.

If the samples are not being analyzed immediately, the samples may be frozen as soon as possible after collection to preserve the integrity of the sample ecology. That is, the sediment, water, and rock/or samples may be frozen as soon after collection as possible to prevent organismal changes within the samples due to the sample being maintained at a different conditions than those at which the sample were collected. Additionally, fixatives and preservatives might be added to the sample prior to freezing. The freezing will induce death, which will provide a snapshot in time so the cold shock response will be captured and not induced by the freezing. For example, the samples may be maintained at a low temperature, such as less than $-60°$ C., or less than $-70°$ C., or less than $-80°$ C., until analyses are performed. In some embodiments, the sample may be maintained at a temperature in the range of $-60°$ C. to $-100°$ C., or from $-60°$ C. to $-80°$ C., until analyses are performed. For samples that are being analyzed in situ, freezing of the samples may not be required. Any remote vehicle of AUV used to collect samples can include the necessary equipment to freeze the sample if sample analysis will not be conducted in real time or near real time.

Once the samples are collected at block 302, the samples are analyzed using various methods to ascertain aspects of the ecology of the sample. For example, the samples may undergo DNA analysis, RNA analysis, metagenomics, proteomics, transcriptomics, lipid analysis, phenotyping, metabolite analysis, organic geochemistry, and inorganic geochemistry analysis, all of which could be done remotely from the region of sample collection or on the AUV. Thus, at block 304 biological material is extracted from the sample. For example, nucleic acids (e.g., DNA and RNA) and proteins are extracted from the sample. Proteins can be extracted from the sample and purified using known techniques. For example, the proteins can be separated from the sample using two dimensional electrophoresis or standard precipitation techniques. The nucleic acids can be extracted from the sample using known techniques. For example, nucleic acids can be extracted from a sediment sample using a sediment DNA extraction technique, such as the MoBio Power Soil DNA extraction kit, or utilizing the method described in U.S. patent application Ser. No. 15/600,161, the disclosure of which is incorporated herein by reference.

At block 306 the extracted proteins are analyzed. For example, the proteins can be analyzed using a shotgun proteomics or protein probe methods. For example, the proteins can be analyzed using a TOF (time of flight) mass spectrometer coupled to a liquid chromatograph or a MALDI (matrix assisted laser desorption/ionization) unit. In some embodiments, the protein samples can be analyzed as mixed sample. In other embodiments, the protein samples can be treated with Thermotogales (for hydrocarbon seeps samples) or Desulfovibrionales (for pipeline samples) specific antibodies and visualized with fluorescence or other means of protein staining.

At block 308 the extracted nucleic acids are analyzed. For example, the extracted nucleic acids can be sequenced, can be identified by fragment size, or can be analyzed using specific DNA/RNA probes. In some embodiments, the nucleic acids can be amplified using specific DNA probes and then be compared to sequencing libraries such as Illumina MiSeq/HiSeq, or with veriosn of ABI Ion Torrent. In some embodiments, whole cells can be stained with RNA specific probes that are attached to a fluorophore, or detection of the fluorophore can be conducted using a confocal or fluorescent microscope.

At block 310, the information from the extracted proteins and/or nucleic acids can be used to detect cold-shock response in thermophiles. This extracted information is then used at block 312 to further detect whether the organisms exhibiting the cold-shock response are indicative of hydrocarbon reservoir or pipelines species, e.g. by assigning taxonomy signatures to the samples to identify family, genus, and/or species of specific Thermotogales present in the sample for hydrocarbon seeps or of specific Desulfovibrionales for hydrocarbon-transporting pipelines. The family, genus, and species specific proteins can be identified by comparing the community lipids and proteins to known standards. Thermotogales (for hydrocarbon seeps samples) or Desulfovibrionales (for pipeline samples) specific DNA sequences can be identified using a bioinformatics pipeline to assign taxonomy to community samples and using a standard sequence database (for example, SILVA, NCBI, GreenGenes) to determine which, if any, Thermotogales (for hydrocarbon seeps samples) or Desulfovibrionales (for pipeline samples) genera are represented in the sample. For specific DNA probes, the presence of an amplicon and then the specific sequence of the amplicon can be compared to known Thermotogales (for hydrocarbon seeps samples) or Desulfovibrionales (for pipeline samples) sequences to identify the specific genus and/or species present. For the fluorescent probes, any fluorescence would indicate that a match was found by the probe, and thus, indicate the presence of the specific genus or species of Thermotogales (for hydrocarbon seeps samples) or Desulfovibrionales (for pipeline samples) being probed for.

The relative abundance of the hydrocarbon reservoir species present in the sample can then be used to predict whether the seep is in fluid communication with a hydrocarbon reservoir or whether the pipeline is leaking at block 314. Also, block 314 can include predicting or determining whether there is a leak in pipeline at a region associated with the sample collection site based on the relative abundance of the species present in the sample relative to the surrounding seawater.

In some embodiments, the community structure of the samples from the hydrocarbon seep or pipeline can be compared to the community structure of reference samples that are not from hydrocarbon seeps or not from leaking pipelines. Thus, it can be verified that the marker (e.g., cold-shock response) abundance in the samples from the seep or the leaking pipeline is greater than the abundance in reference samples. If the markers are present and sufficiently abundant then the markers can be used to indicate that the sample did in fact come from a hydrocarbon seep or from a leaking pipeline. For example, a reference sample may be obtained at a location that is at least 200 meters, or at least 250 meters, or at least 300 meters, or at least 350 meters, or at least 400 meters, or at least 450 meters, or at least 500 meters away from the center of the location where the seep is emanating from the surface, and in some embodiments, less than 2000 meters, or less than 1750 meters, or less than 1500 meters, or less than 1250 meters, or less than 1000 meters away from the location where the seep is emanating from the surface. Similarly, a reference sample may be obtained at a location that is at least 200 meters, or at least 250 meters, or at least 300 meters, or at least 350 meters, or at least 400 meters, or at least 450 meters, or at least 500 meters away from any location in the length of a pipeline, and in some embodiments, less than 2000 meters, or less than 1750 meters, or less than 1500 meters, or less than 1250 meters, or less than 1000 meters away from any location in the length of a pipeline The indicators developed herein can be used to identify seeps that are likely linked to reservoirs. Seeps that are fed from shallow deposits will not have the same set of characteristics (e.g., no cold-shock response). Similarly, the indicators developed here can be used to identify hydrocarbon leaking from a corroded or damaged pipeline, while unaffected pipelines will not have the same characteristic (e.g., no cold-shock response).

In addition to conventional exploration, the methodologies described herein can also provide critical information during unconventional hydrocarbon exploration and development. Specifically, oil shale, shale gas and oil sand systems have properties that vary as a function of temperature, pressure, hydrocarbon type, inorganic mineralogy and chemistry. These properties can impact the predicted economic volumes that can be obtained from these unconventional reservoirs. Oil shale and shale gas are settings where the source rock is the reservoir, which means hydrocarbon migration is limited. Microbial products and biomarkers may help identify in situ pressures, temperatures and variations in hydrocarbon types across a geologic area of interest. Bioindicators beyond the usual 16S rRNA gene allow for more flexibility when detecting subsurface or leaked pipeline species. Proteins, DNA, RNA, and metabolites will travel farther through rock and sediment than cells due to their size. Although this data would be obtained from test well samples, there is still an opportunity to calibrate basin and petroleum system models and constrain fluid or gas properties to better identify and extract resources. The role of indigenous microbial communities in controlling or altering the interface between mineral-hydrocarbon-aqueous phases may apply for the oil shale scenario, but are perhaps even more critical for oil sands. Typically, added microbial or fungal byproduct slurries are used to help alter subsurface conditions. This alteration is accomplished by the formation or addition of surfactants or by changing the hydrocarbon properties or composition. For example, converting viscous hydrocarbons to methane can help facilitate hydrocarbon extraction. The methodologies and techniques described herein may help optimize selection of zones, facies, or formations that have indigenous communities that may already produce or enhance hydrocarbon extraction without additional treatments. Specifically in oil sands, samples from multiple zones are combined to produce an aggregate that is then processed to remove the oil. If the proportions of these different materials are adjusted to include those that have increased natural surfactants, then this may increase the overall yield obtained from the homogenized aggregate.

Furthermore, data from one or more seeps can be collected, and the fluid communications between the one or more seeps and the hydrocarbon reservoir can be included in a geologic model. The geologic model can be used to generate subsurface images and to carry out hydrocarbon management operations. For example, if multiple seeps are analyzed, then the updated geological model can indicate multiple different types of seeps and fluid communication paths in the subsurface, which can further inform hydrocarbon explorers about the subsurface and improve exploration operations by identifying locations to drill exploration wells.

Figure 4:
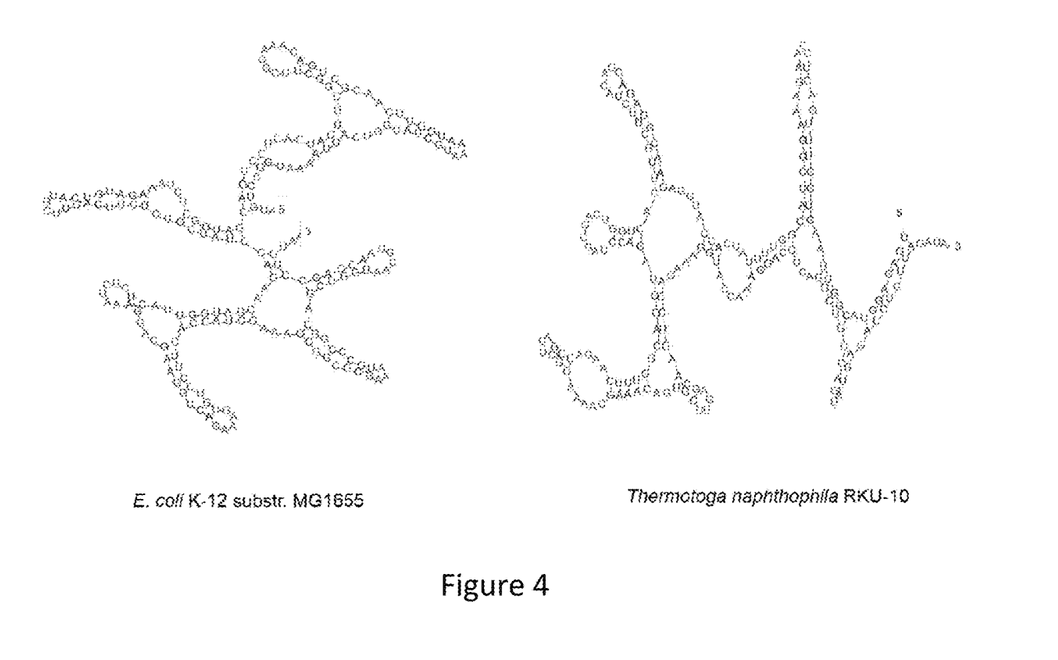
FIG. 4 illustrates comparability of minimum free energy of the RNA secondary structure for two organisms, one of which is a hyperthermophile.

FIG. 4 illustrates comparability of minimum free energy of the RNA secondary structure for two organisms. The minimum free energy structure of a single stranded nucleic acid sequence is the calculated secondary structure with the lowest possible value of free energy. Secondary structures are formed in single-stranded nucleic acids, like RNA, when matching nitrogen bases (A:U and C:G) of nucleotides bind to form portions of double stranded nucleic acid. Formation of secondary structures improve the stability of the nucleic acid and/or regulate protein synthesis. In theory, the lower the free energy, the more likely is the structure to form. Similarity in RNA secondary structures and minimum free energy are indirect evidence of similar properties. In this figure, matching complementary nucleotides are shown as paired strands, while the others are unmatched loops. The example from FIG. 4 shows similarities between the cspA from *Escherichia coli*, for which the secondary structure has been shown to be correlated to the RNA stability at temperature lower than the optimum (37° C., e.g., Fang et al., Molecular Microbiology (1997) 23(2), 355-364), and *Thermotoga naphtophila*, which possesses a much higher temperature optimum (80° C.). Both prokaryotes and eukaryotes exhibit a cold-shock response upon an abrupt temperature downshift. Cold-shock proteins are synthesized to overcome the deleterious effects of cold shock. CspA, the major cold-shock protein of *E. coli*, has recently been studied with respect to its structure, function and regulation at the level of transcription, translation and mRNA stability. Homologues of CspA are present in a number of organisms (see, Phadtare, et al., Cold-shock response and cold-shock proteins, Current Opinion in Microbiology, Vol. 2, Issue 2, pp. 175-180 (April 1999)). The secondary structures and minimum free energy were calculated using the "maplot" function as implemented in the Bioinformatics toolbox of Matlab.

Figure 5:
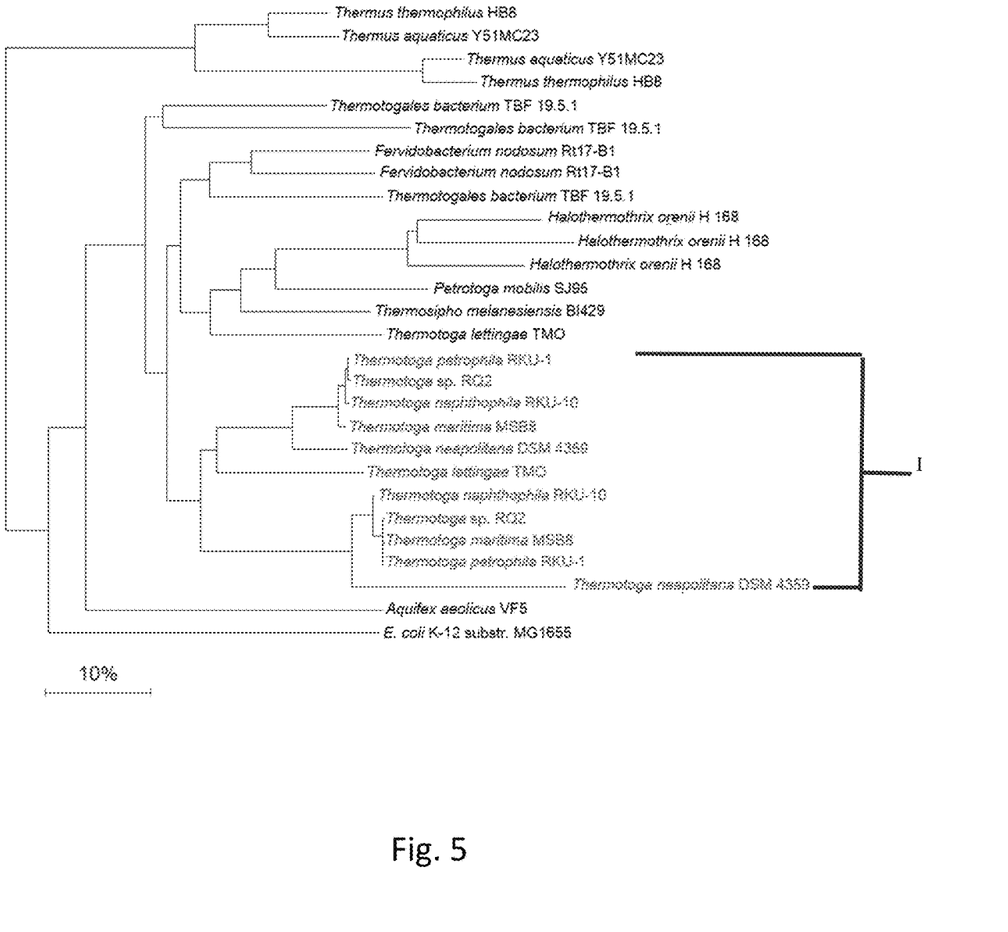
FIG. 5 illustrates phylogenetic tree showing that CspA-like proteins are widespread across thermophiles.

FIG. 5 illustrates phylogenetic tree showing that cspA-like proteins are widespread across thermophiles. This neighbor-joining tree was built using cspA-like DNA sequences from mainly thermophiles and hyperthermophiles obtained from publicly available databases (e.g., NCBI). Scale bar represent 10% sequences similarity. Group I of *Thermotoga* indicate possible monophyletic origin for that group (i.e., same ancestor). The tree was calculated using the "PhyLoTree" function as implemented in the Bioinformatics toolbox of Matlab. As a particular example, ascertaining that a particular hydrocarbon seep is connected to a subsurface hydrocarbon reservoir is an important piece of information that can be used to reduce the risks associated with exploring for oil and gas. Using microbial information that indicates a microbe came from a much warmer environment combined with the previous association of that microbe to hydrocarbon reservoir will improve the confidence that the seeped fluids are in fact connected to a subsurface accumulation of hydrocarbons. That is, the methodologies described herein allow one to focus exploration efforts and can ultimately affect ones decision on if, when, and where to drill an exploration well.

Figure 6:
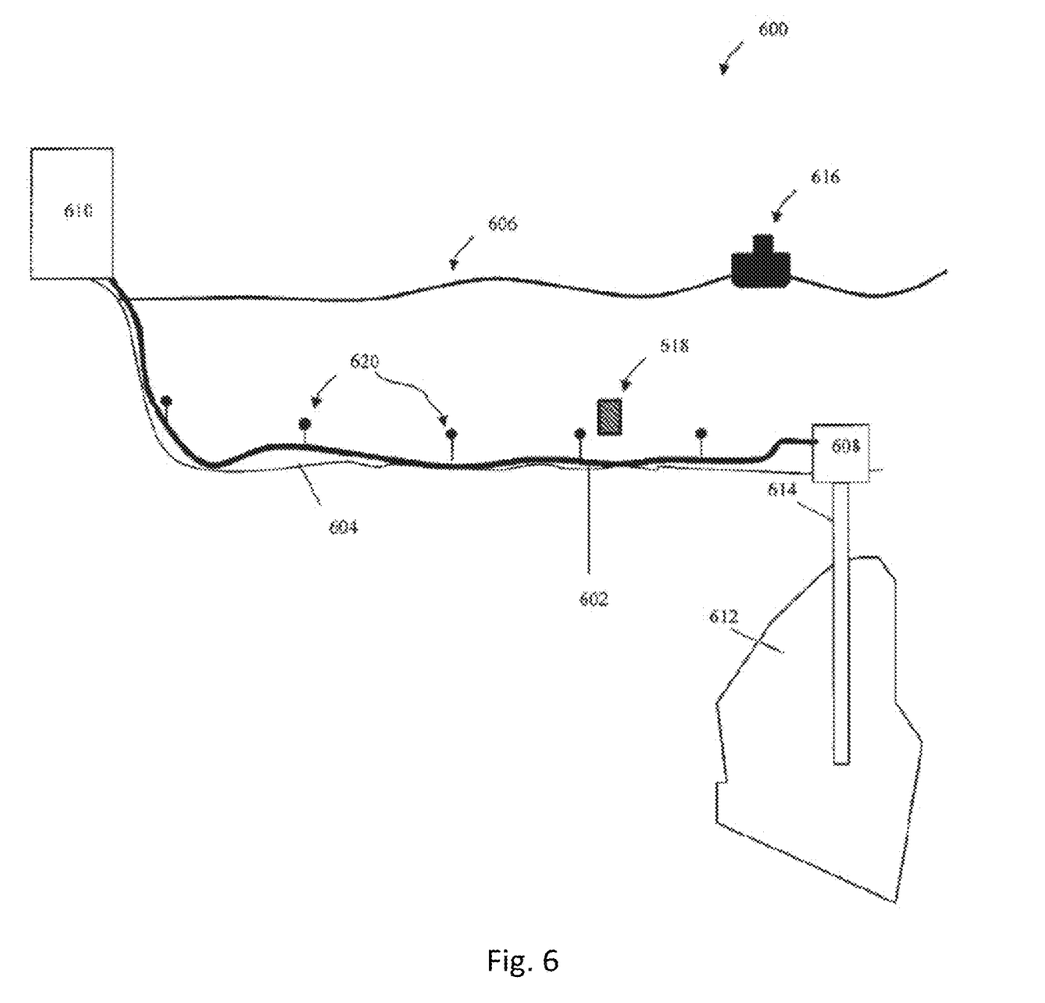
FIG. 6 illustrates an exemplary leak detection system.

FIG. 6 is a diagram of an exemplary leak detection system 600 in accordance with an exemplary embodiment of the present technological advance. In this configuration, a pipeline 602 is disposed on the floor 604 of a body of water 606. The pipeline 602 provides a fluid flow path from a wellhead 608 to a fluid processing facility 610. The wellhead 608 provides fluid access (e.g., hydrocarbons and/or other fluids that may be transported via tubulars) to a reservoir 612 via a wellbore 614. The access to and operation of the wellbore 614, wellhead 608 and fluid processing facility 610 are known to those skilled in the art.

To monitor the pipeline 602, a marine vessel 616 (which can be equipped with an automatic sample collection and/or analysis device) can be utilized to deploy an ALT 618. This AUV 6M can be any underwater vehicle that includes a sample collection mechanism and/or sample analysis equipment (sensors, computer, microarrays). The navigation component of the AUV 618 may include a GPS component, and wireless guidance component, a mapping component and motion sensor components navigation sensors and/or motor propeller speedometer) for navigating the body of water 606. The AUV may include an obstacle detection component. When an obstacle is detected, the obstacle detection component may compare the obstacle to the apriori map, which may be stored in memory. If it is an obstacle not marked in the previous apriori map, then the location of the obstacle may be stored in the apriori map and the map gets updated. The wireless guidance component may receive signals from the pipeline wireless guidance transmitters 620 disposed along the pipeline 602. As the AUV 618 moves along the pipeline, the measurement components of the AUV 618 may be utilized to collect samples to determine if the pipeline has a leak in accordance with the teachings of the present technological advancement. The temperature of the oil or gas within the pipeline will be much higher than the temperature of the surrounding seawater. If a microbe within the oil or gas escapes from the pipeline, then a cold shock response can result. AUV 618 can collects samples of water that include the leaked microbes with the cold shock response carry them back to vessel 616 for analysis or perform analysis (such as metabolomics) of the samples on board the AUV and wirelessly communicate the results to vessel 616. Also, samples can be collected at or near multiple segments of the pipeline in order to more closely locate a source of the leak. Furthermore, an AUV with appropriately programmed computer navigation can establish a search vector in order to find leaks. As the AUV analyses various seawater samples, the computer on the AUV can create a real time map of relative abundance of cold-shock response markers, which can be for real time pipeline integrity surveillance and leak detection. The leak detection method of the present technological advancement can provide advanced warning (i.e., the smaller size of the cold shock response markers (whether they be DNA, RNA, or metabolites, may escape from micro fissures in the pipeline) regarding pipeline integrity so remedial measure can be implemented as needed.

Although the disclosed methodologies and techniques may be applied advantageously to oil and gas exploration activities, there are other ways in which said methodologies and techniques may be used, such as microbially enhanced oil recovery due to production of methane via methanogenesis, exopolysaccharides and enzymes causing changes fluid properties (e.g., viscosity), addition of microbial slurries to enzyme-activated proppants, and surfactants that change the interface between the hydrocarbons and minerals (e.g., emulsion breakers), reducing waxy components and increasing flow. In some cases the need to obtain microbial information is related to the potential for scale formation, reservoir souring, and pipeline corrosion if left untreated. Although reservoir fluid flow applications are based primarily on introducing biological tags downhole, critical information about how these biotechnology systems work may provide necessary insight into facies-specific properties and behavior, such as zones with unique indigenous ecology. From this type of data set, there is potential to target specific subsurface conditions or intervals and therefore optimize site selection based on a particular suite of desired properties. In all of these examples, a toolkit that appropriately identifies inherent and diagnostic information linked to ecologic and geochemical conditions in the subsurface will be helpful to de-risk some zones considered for exploring unconventional hydrocarbon plays or systems.

The disclosed methodologies and techniques provide a method that combines a full suite of geochemical and biological tools to identify organisms, their by-products, metabolites and the like that may be transported from the reservoir to the air-sediment or water-sediment interface with the fluids and hydrocarbons. This also includes differentiation of organisms living in association with the hydrocarbons, or related transported materials, at the interface that may shed light on hydrocarbon quality or changes therein due to transport and any degradation that may occur along the migration pathway. If extracellular DNA and other biomarkers are released within the reservoir, there is time for equilibration, reaction and association with reservoir geochemistry that may provide characteristic compositions that are retained during transport to surface and therefore provides more opportunity for assessing subsurface conditions. For example, the disclosed methodologies and techniques that combine metagenomic analysis, proteomics, lipid analysis, molecular geochemistry, biomarker and/or isotopic information will provide more information about the reservoir, ecology, and hydrocarbons and fluids therein than could be acquired from other approaches, such as PCR, quantitative PCR (qPCR), microarray or culturing methods alone.

The invention claimed is:

1. A method of determining whether a hydrocarbon seep emanating from a seafloor is in fluid communication with a hydrocarbon reservoir comprising:
    (a) obtaining a field sample near the hydrocarbon seep, wherein the field sample is obtained from a location that is within a radius of 150 meters from a center location where the hydrocarbon seep is emanating from the seafloor;
    (b) extracting one or more of proteins or nucleic acids from the field sample;
    (c) analyzing the extracted proteins or nucleic acids to identify thermophiles within the field sample that exhibit cold-shock signatures, wherein the cold-shock signatures are RNA secondary structures in which a portion of matching nitrogen nucleotide bases are bound (A:U and C:G) and a portion of matching nitrogen nucleotide bases are unbound, the cold-shock signatures due to the thermophiles experiencing an abrupt temperature downshift below an optimum temperature;

(d) analyzing the cold-shock response thermophiles identified in step c to identify thermophile signatures that are indicative of hydrocarbon reservoir species, the hydrocarbon reservoir species being selected from the group consisting of Thermotogales, Desulfovibrionales, and any combination thereof; and (e) determining that the hydrocarbon seep is in fluid communication with the hydrocarbon reservoir based on the abundance of the cold-shock signatures in the field sample near the hydrocarbon seep compared to the surrounding environment, wherein if the cold-shock signatures are at least double compared to the surrounding environment it is determined that the hydrocarbon seep is in fluid communication with the hydrocarbon reservoir.

2. The method of claim 1, wherein the field sample is obtained from a water column near the hydrocarbon seep.

3. The method of claim 1, wherein the field sample is a sediment sample obtained from the seafloor near the hydrocarbon seep.

4. The method of claim 1, wherein the radius is within 10 meters from the center location where the hydrocarbon seep is emanating from the seafloor.

5. The method of claim 1, wherein the radius is within 3 meters from the center location where the hydrocarbon seep is emanating from the seafloor.

6. The method of claim 1, wherein the nucleic acid analysis comprises RNA analysis.

7. The method of claim 1, wherein steps a-e are performed for multiple hydrocarbon seeps, and the method further comprises:

(a) determining multiple paths of fluid communication between the hydrocarbon reservoir and the seafloor;

(b) including the paths in a geologic model;

(c) generating a subsurface image from the geologic model; and (d) causing a well to be drilled at a location derived from the geologic model.

8. A method of monitoring a hydrocarbon pipeline disposed in a body of water, the method comprising:

(a) obtaining a field sample near the pipeline, wherein the field sample is obtained from a location that is within a radius of 150 meters from a location along a length of the pipeline;

(b) extracting nucleic acids from the field sample;

(c) analyzing the extracted nucleic acids to identify thermophiles within the field sample that exhibit cold-shock signatures, wherein the cold-shock signatures are RNA secondary structures in which a portion of matching nitrogen nucleotide bases are bound (A:U and C:G) and a portion of matching nitrogen nucleotide bases are unbound, the cold-shock signatures due to the thermophiles experiencing an abrupt temperature downshift below an optimum temperature, the hydrocarbon species being selected from the group consisting of Thermotogales, Desulfovibrionales, and any combination thereof;

(d) analyzing the cold-shock response thermophiles identified in step c to identify thermophile signatures that are indicative of hydrocarbon reservoir species, the hydrocarbon species being selected from the group consisting of Thermotogales, Desulfovibrionales, and any combination thereof; and (e) determining that the pipeline is leaking based on the abundance of the cold-shock signatures in the sample near the pipeline compared to the surrounding environment, wherein if the cold-shock signatures are at least double compared to the surrounding environment it is determined that the pipeline is leaking.

9. The method of claim 8, wherein steps (a)-(e) are performed by an autonomous underwater vehicle including an automatic sample collection and analysis device.

10. The method of claim 8, wherein step (a) is performed by an underwater vehicle, and the method further comprises:

(a) collecting a plurality of samples along the pipeline with the underwater vehicle; and (b) generating, with a computer, a map of relative amounts of cold-shock response markers for various underwater locations.

* * * * *